United States Patent [19]

Franckowiak et al.

[11] Patent Number: 4,764,516
[45] Date of Patent: Aug. 16, 1988

[54] MIXTURES OF OPTICALLY ACTIVE NITRODIHYDROPYRIDINES ACTIVE ON THE CIRCULATORY SYSTEM

[75] Inventors: Gerhard Franckowiak, Wuppertal; Rolf Grosser, Leverkusen; Günter Thomas, Wuppertal; Matthias Schramm, Cologne; Rainer Gross, Wuppertal, all of Fed. Rep. of Germany

[73] Assignee: Bayer Aktiengesellschaft, Leverkusen, Fed. Rep. of Germany

[21] Appl. No.: 806,071

[22] Filed: Dec. 6, 1985

[30] Foreign Application Priority Data

Dec. 22, 1984 [DE] Fed. Rep. of Germany ....... 3447169

[51] Int. Cl.⁴ ................. A61K 31/455; A61K 31/505
[52] U.S. Cl. ..................... 514/256; 514/332; 514/334; 514/352; 544/333; 546/257; 546/258; 546/263; 546/310; 546/312
[58] Field of Search ............... 546/310; 514/352, 256, 514/332, 334

[56] References Cited

U.S. PATENT DOCUMENTS

| | | | |
|---|---|---|---|
| 4,248,873 | 2/1981 | Bossert et al. | 546/284 |
| 4,264,611 | 4/1981 | Berntsson et al. | 546/321 |
| 4,492,703 | 1/1985 | Goldmann et al. | 546/321 |
| 4,532,248 | 7/1985 | Franckowiak et al. | 514/89 |
| 4,678,796 | 7/1987 | Taylor et al. | 546/321 |

FOREIGN PATENT DOCUMENTS

| | | |
|---|---|---|
| 0002208 | 6/1979 | European Pat. Off. . |
| 0030343 | 6/1981 | European Pat. Off. . |
| 0039863 | 11/1981 | European Pat. Off. . |
| 0071819 | 2/1983 | European Pat. Off. . |

OTHER PUBLICATIONS

Thomas, G. et al., Journal of Cardiovascular Pharmacy 6 1170–1176 (1984).
Bolger, G. T. et al., Chemical Abstracts 102: 197756e.
Takenaka, T. et al., Japan J. Pharmacol. 32, 665–670 (1982).

Primary Examiner—Mary C. Lee
Assistant Examiner—Dale A. Bjorkman
Attorney, Agent, or Firm—Sprung Horn Kramer & Woods

[57] ABSTRACT

Pure enantiomers of 5-nitrodihydropyridine of the formula

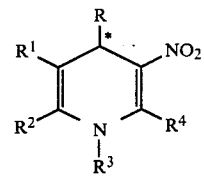

are mixed, wherein one of the enantiomers has a high vasodilative action and a low negative inotropic activity on heart muscle, the other enantiomer has a low vasoconstrictive action and a high positive inotropic activity on heart muscle, the mixture being high in vasodilative activity and in positive inotropic activity on heart muscle.

7 Claims, No Drawings

MIXTURES OF OPTICALLY ACTIVE NITRODIHYDROPYRIDINES ACTIVE ON THE CIRCULATORY SYSTEM

The present invention relates to (+)- and (−)-enantiomers of 5-nitrodihydropyridines of the general formula I

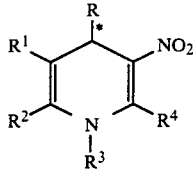

in which R represents heteroaryl, or represents aryl (6 or 10 C atoms) which is optionally monosubstituted or polysubstituted, identically or differently, by halogen, nitro, cyano, carboxyl, hydroxyl, alkoxycarbonyl (up to 4 C atoms), amino, monoalkylamino or dialkylamino (in each case up to 3 C atoms), sulphonamido or —SO$_2$—alkyl (up to 4 C atoms), by optionally halogen-substituted alkyl or alkoxy (in each case up to 6 C atoms), or by the group

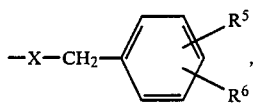

wherein
X represents oxygen, sulphur or NR$^7$,
R$^7$ represents hydrogen, alkyl (up to 3 C atoms) or phenyl and
R$^5$ and R$^6$ are identical or different and represent hydrogen, nitro, cyano or alkyl, alkoxy, alkylthio, halogenoalkyl, halogenoalkoxy or halogenoalkylthio (alkyl in each case up to 6 C atoms),
R$^1$ represents hydrogen or the group CO$_2$R$^8$
wherein
R$^8$ represents hydrogen or linear or branched alkyl (up to 10 C atoms) which can be interrupted by one or two oxygen and/or sulphur atoms in the chain and which is optionally substituted by phenyl, nitro, halogen, hydroxyl, cyano, sulphonamido, —SO$_2$-alkyl (up to 4 C atoms), carboxyl, alkoxycarbonyl (up to 4 C atoms), pyridyl or by an amino group, it being possible for this amino group to be substituted by one or two substituents from the series alkyl (up to 4 C atoms), aryl (6 or 10 C atoms) or aralkyl (7–14 C atoms),
R$^2$ and R$^4$ can be identical or different and represent cyano or linear or branched alkyl (up to 6 C atoms) which is optionally substituted by hydroxyl, cyano, halogen, aryl (6 or 10 C atoms), carboxyl or alkoxycarbonyl (up to 6 C atoms) and
R$^3$ represents hydrogen or linear or branched alkyl (up to 6 C atoms),
and to salts thereof.

Preferred (+)- and (−)-enantiomers of the general formula I are those in which R represents pyrryl, furyl, thienyl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl or quinoxalyl, or represents phenyl which is optionally monosubstituted or disubstituted, identically or differently, by fluorine, chlorine, bromine, nitro, cyano, carboxyl, alkoxycarbonyl (up to 2 C atoms), —SO$_2$-alkyl (up to 2 C atoms) or by optionally halogen-substituted alkyl or alkoxy (up to 5 C atoms), or represents the group

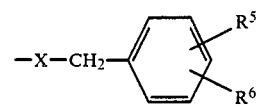

wherein
X represents oxygen or sulphur and
R$^5$ and R$^6$ are identical or different and represent hydrogen, nitro, cyano or alkyl, alkoxy, alkylthio, halogenoalkyl or halogenoalkoxy (in each case up to 4 C atoms),
R$^1$ represents hydrogen or the group CO$_2$R$^8$
wherein
R$^8$ represents hydrogen or linear or branched alkyl (up to 8 C atoms) which can be interrupted by one or two oxygen and/or sulphur atoms in the chain and which is optionally substituted by phenyl, nitro, one or more fluorine, chlorine, bromine, hydroxyl, cyano, —SO$_2$-alkyl (up to 2 C atoms), alkoxycarbonyl (up to 2 C atoms) or pyridyl groups or by an amino group, it being possible for this amino group to be substituted by one or two substituents from the series alkyl (up to 3 C atoms), phenyl or benzyl,
R$^2$ and R$^4$ represent cyano or linear or branched alkyl (up to 4 C atoms) which is optionally substituted by hydroxyl, fluorine, chlorine, phenyl or alkoxycarbonyl (up to 4 C atoms) and
R$^3$ represents hydrogen or linear or branched alkyl (up to 4 C atoms),
and salts thereof.

(+)- and (−)-enantiomers of the general formula I which are particularly preferred are those in which R represents furyl, thienyl, pyridyl or pyrimidyl, or represents phenyl which is optionally mono-substituted or disubstituted, identically or differently, by fluorine, chlorine, nitro or cyano or by alkyl or alkoxy (in each case up to 4 C atoms) which is optionally substituted by one or more fluorine atoms, or by the group

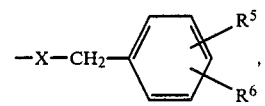

wherein
X represents oxygen or sulphur and
R$^5$ and R$^6$ are identical or different and represent hydrogen, nitro, cyano or alkyl, alkoxy, alkylthio, halogenoalkyl or halogenoalkoxy (in each case up to 2 C atoms), and halogen preferably represents one or more fluorine atoms,
R$^1$ represents hydrogen or the group CO$_2$R$^8$
wherein
R$^8$ represents hydrogen or linear or branched alkyl (up to 6 C atoms) which can be interrupted by an oxygen and/or sulphur atom in the chain and which is optionally substituted by phenyl, nitro or one or more fluorine, chlorine, cyano, benzylmethylamino or pyridyl groups,
R$^2$ and R$^4$ represent methyl or ethyl which is optionally substituted by hydroxyl or one or more fluorine, phenyl or alkoxycarbonyl (up to 2 C atoms) groups and R³ represents hydrogen or methyl or ethyl,
and salts thereof.

The substances according to the invention can be in the form of their salts. These are, in general, salts with inorganic or organic acids. The physiologically acceptable salts of the substances according to the invention with organic or inorganic acids are preferred. Examples which may be mentioned are hydrochlorides, hydrobromides, bisulphates, sulphates, hydrogenphosphates, acetates, maleates, fumarates, citrates, tartrates or benzoates.

The (−)-enantiomers of the general formule (I) are very particularly preferred.

The (+)- and (−)-enantiomers, according to the invention, of the general formula (I) are prepared by reacting the optically active aminocrotonic acid esters of the general formula (II)

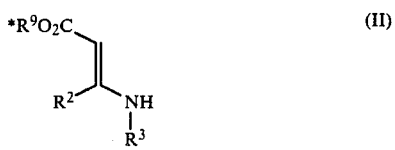

in which
R² and R³ have the meaning indicated above and
*R⁹ represents a chirally uniform 2-methoxy-2-phenylethyl radical,
with ylidene compounds of the general formula (III)

if appropriate in the presence of water or inert organic solvents, then separating by customary methods the diastereomers obtained in this reaction, because of the two possible different configurations at the C₄ atom of the dihydropyridine ring, and either transesterifying the resulting 1,4-dihydropyridines having a chiral ester grouping of the general formula IV

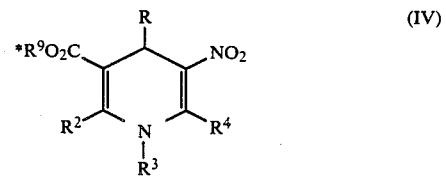

in which R, R¹, R², R³, R⁴ and *R⁹ have the meaning indicated above, in accordance with customary methods by replacing the chiral radical *R⁹ by a non-chiral radical R⁸ (≠ hydrogen), or hydrolyzing the resulting 1,4-dihydropyridines having a chiral ester grouping of the general formula IV to give compounds in which R⁸=hydrogen and then, if appropriate, re-esterifying the latter or decarboxylating them to give compounds in which R¹=H, (+)- and (−)-enantiomers of the general formula I being obtained in each case.

The starting materials of the formula (II) and (III) are known or can be prepared by known methods (see A. Dornow, W. Sassenberg, Liebigs Ann. Chem. 602, 14 (1957); or S. A. Glickmann, A. C. Cope, J. Am. Chem. Soc., 67, 1017 (1945)).

The substances of the formula (IV) are new and can be prepared in the manner indicated.

Suitable diluents are water or any inert organic solvent. These preferably include alcohols, such as methanol, ethanol, propanol or isopropanol, ethers, such as diethyl ether, dioxane, tetrahydrofuran or glycol monoethyl ether, glacial acetic acid, pyridine, dimethylformamide, acetonitrile, dimethyl sulphoxide or hexamethylphosphoric acid triamide.

The reaction temperatures can be varied within a fairly wide range. In general, the reaction is carried out within a range from 10° C. to 200° C., preferably from 20° C. to 150° C.

The reaction can be carried out under normal pressure but also under elevated pressure. In general, the reaction is carried out under normal pressure.

The compounds of the formula (IV) formed in accordance with the process indicated above differ, as diastereomers, in their physical and chemical properties and can, therefore, be separated from one another by means of known methods. The following may be mentioned as preferable methods of separation: recrystallization from inert solvents or thin layer, column or high pressure liquid chromatography.

The necessary hydrolysis or transesterification of the chirally uniform compounds IV is preferably effected via alkaline hydrolysis or alcoholysis, if appropriate in the presence of an inert solvent, using as the reagent R⁸O⁻, wherein R⁸ has the meaning indicated above.

Solvents suitable for this hydrolysis or transesterification are water or any inert organic solvent or mixtures thereof. These preferably include alcohols, such as methanol, ethanol. propanol or isopropanol, ethers such as dioxane, tetrahydrofuran, glycol monoethyl ether of glycol dimethyl ether, or dimethylformamide, dimethyl sulphoxide, acetonitrile, pyridine or hexamethylphosphoric acid triamide.

The reaction temperatures can be varied within a fairly wide range. In general, the reaction is carried out between 20° and 150° C., preferably at approximately 50° to 100° C.

The hydrolysis or transesterification can be carried out under normal pressure, but also under elevated pressure. In general, the reaction is carried out under normal pressure.

Suitable alcoholysis or hydrolysis reagents R⁸O⁻ are the customary bases. It is preferable to employ alkali or alkaline earth metal hydroxides, such as, for example, sodium hydroxide, potassium hydroxide, calcium hydroxide or barium hydroxide, or alkali metal alcoholates, such as, for example, sodium methylate or ethylate or potassium methylate or ethylate. It is also possible to use a mixture of bases. In carrying out the hydrolysis or alcoholysis, the bases are in each case employed in molar amounts or in a slight excess.

The decarboxylation of the compounds in which R¹=COOH to give compounds in which R¹=H is effected in a customary manner. It is preferable to carry out thermal decarboxylation, if appropriate in the absence of an acid catalyst, by heating the approprite carboxylic acid with or without a solvent.

Suitable solvents for the decarboxylation are water and inert organic solvents or mixtures. These preferably include water, alcohols, such as, for example, methanol, ethanol, propanol, glycol or diglycol, ethers, such as dioxane, tetrahydrofuran, glycol monoethyl ether, glycol dimethyl ether or diethylene glycol dimethyl ether, or dimethylformamide, dimethyl sulphoxide, acetonitrile, glacial acetic acid, hexamethylphosphoric acid triamide, toluene or xylene.

The reaction temperatures can be varied within a fairly wide range. In general, the reaction is carried out between 40° and 200° C., preferably between 60° and 150° C.

The decarboxylation can be carried out under normal pressure, under elevated pressure or under reduced pressure. In general, it is carried out under normal pressure. The customary inorganic or organic acids can be used as catalysts. These preferably include hydrogen halide acids, such as HCl or HBr, sulphuric acid, phosphoric acid or organic acids, such as acetic acid, formic acid, toluenesulphonic acid or methanesulphonic acid.

The re-esterification of the carboxylic acids according to the invention ($R^8$=H) is effected by known methods, if appropriate via a reactive acid derivative such as, for example, activated esters, hydroxysuccinimide esters, acid imidazolides or mixed anhydrides, or by reaction with dicyclohexylcarbodiimide.

The customary organic solvents are suitable for this purpose. These preferably include hydrocarbons, such as methylene dichloride, chloroform, carbon tetrachloride or 1,2-dichloroethane, ethers, such as diethyl ether, dioxane, tetrahydrofuran or 1,2-dimethoxyethane, aromatic hydrocarbons, such as toluene or xylene, acetonitrile, nitromethane, dimethylformamide, hexamethylphosphoric acid triamide, pyridine or ethyl acetate.

The reaction temperatures in this case can be varied within a fairly wide range. In general, the reaction is carried out within a range from −70° C. to +60° C., preferably from −50° C. to +40° C.

The re-esterification can be carried out under normal pressure, but also under elevated pressure. In general, it is carried out under normal pressure.

In carrying out the reaction, the ratio of the reactants is immaterial. However, it has proved expedient to employ the corresponding alcohol in an excess of up to 20 times molar, preferably up to 10 times molar.

The enantiomers of the general formula (I) are also obtained if the corresponding racemates are separated into the (+)- and (−)-enantiomers of the general formula (I) by means of suitable methods of separation, if desired using optically active materials, by means of, for example, thin layer, column or high pressure liquid chromatography.

It is known that racemic nitrodihydropyridines intensify the contractile force-boosting positively inotropic action on heart muscle. Moreover, it is known that the pharmacological activity of the isolated enantiomers differs from that of the racemate.

Thus, one of the isomers often has a stronger action, and the other a weaker action, than the racemate. It was not foreseeable that the enantiomers according to the invention would differ completely in their action. Surprisingly, one enantiomer in each case, whose absolute configuration is that of formula V

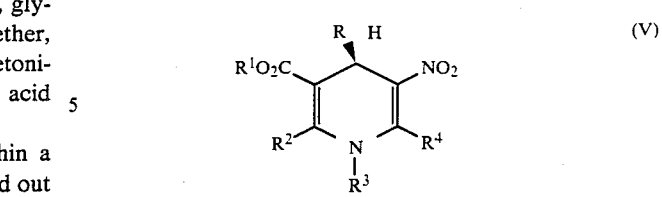

has a vasodilative action and is negatively inotropic on heart muscle, while the other enantiomer, whose absolute configuration is that of formula VI

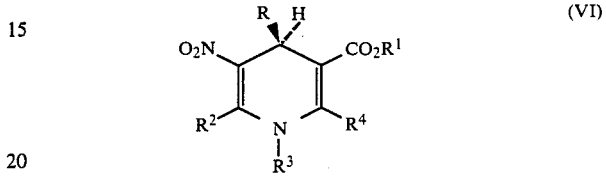

is vasoconstrictive and positively inotropic on heart muscle.

The (−)-enantiomers of all the preparative examples are in accordance with the absolute configuration of formula VI but the optical rotation of other (−)-enantiomers according to the invention have the configuration of formula V.

In detail, the following principal actions were demonstrated for the vasodilative enantiomers in an animal experiment:

1. On parenteral, oral and perlingual administration the compounds produce a distinct and long-lasting dilation of the coronary vessels. They influence or modify the heart metabolism in the sense of an energy saving.

2. The excitability of the nervous impulse generation and stimulus conduction system within the heart is reduced, so that an anti-fibrillation action demonstrable in therapeutic doses.

3. The tonus of the smooth muscle of the vessels is greatly reduced under the action of the compounds. This vascular-spasmolytic action can occur in the entire vascular system or can manifest itself more or less isolatedly in circumscribed vascular zones (such as, for example, the central nervous system). Accordingly, the compounds are also suitable for use as cerebral therapeutic agents.

4. The compounds lower the blood pressure of normal tonic and hypertonic animals and can accordingly be used as anti-hypertensive agents.

5. Compounds have powerful muscular-spasmolytic actions which manifest themselves on the smooth muscle of the stomach, intestinal tract, urogenital tract and respiratory system.

Because of these properties, these enantiomers according to the invention are particularly suitable for the prophylaxis and therapy of acute or chronic ischaemic heart disorders and for the treatment of cerebral and peripheral circulatory disturbances.

The optical antipodes to these enantiomers have a positive inotropic action and accordingly exhibit an unforeseeable and valuable pharmacological spectrum of action. They can serve as cardiotonics to improve the heart contractivity. In addition, they can be employed as anti-hypotonics, to reduce the blood sugar level, to detumesce mucous membranes and to influence the salt balance and fluid balance.

The invention moreover relates to a new active compound combination containing (−)-enantiomers of the formula (I) (component X) and (+)-enantiomers of the formula (I) (component Y).

At suitable ratios of the components X and Y, the combination shows a completely surprising action profile: they are positively inotropic and vasodilative, especially coronary-dilative.

Per part by weight of component X, 0.01–1,000 parts by weight, preferably 0.1–50 parts by weight, of component Y can be employed.

In case of a 1:1 mixture not the racemate of compound X and Y is meant, which occurs if no optically active starting material in the preparation is used. In case of a 1:1 mixture a combination of different enantiomers is meant.

The combinations may be prepared by dissolving the individual components in inert solvents which dissolve them, and subsequently mixing the solutions. As examples of inert solvents, alcohols such as ethanol or glycols such as polyethylene glycol, or dimethylsulphonide may be mentioned.

The active compound combination according to the invention can be used to combat illnesses, in particular circulatory disorders.

The cardiac and vascular actions of the enantiomers according to the invention and of the combination were found on the isolated perfused heart of the guinea pig (modified according to Opie, L., J. Physiol. 180 (1965) 529–541). For this purpose, the hearts of albino guinea pigs weighing 250 to 350 g are used. The animals are killed by a blow to the head, the thorax is opened, a metal cannula is tied into the exposed aorta and the left auricle is opened. The heart is removed together with the lungs from the thorax and is connected via the aorta cannula to the perfusion apparatus, while the perfusion is running. The lungs are severed off at the lung roots. The perfusion medium used is Krebs-Henseleit solution (118.5 mmol of NaCl/liter, 4.75 mmol of KCl/liter, 1.19 mmol of $KH_2PO_4$/liter, 119 mmol of $MgSO_4$/liter, 25 mmol of $NaHCO_3$/liter, and 0.013 mmol of NaEDTA/liter), the $CaCl_2$ concentration of which is varied according to requirements but is as a rule 1.2 mmol/liter. 10 mmol of glucose/liter are added as an energy-supplying substrate. Before perfusion, the solution is filtered to remove any particles. The solution is gassed with carbogen (95% of $O_2$, 5% of $CO_2$ to maintain the pH value of 7.4). The hearts are perfused at constant flux (10 ml/min) at 32° C., by means of a peristaltic pump.

To measure the heart function, a liquid-filled latex balloon which is connected via a liquid column to a pressure sensor is introduced through the left auricle into the left ventricle and the isovolumetric contractions are recorded on a high-speed pen recorder.

The perfusion pressure is recorded by means of a pressure sensor which is connected to the perfusion system upstream of the heart. Under these conditions, a reduction in perfusion pressure indicates a coronary dilation and an increase in the left ventricular pressure amplitude indicates an increase in heart contractility. The enantiomers according to the invention, or their combinations, in suitable dilutions are infused into the perfusion system a short way upstream of the isolated heart.

Table 1 shows the action of some stereoisomers on the contractility and coronary resistance of the isolated heart of the guinea pig.

Isomer 1: (+)-[Methyl 1,4-dihydro-2,6-dimethyl-5-nitro-4-(2-trifluoromethylphenyl)-pyridine-3-carboxylate]

Isomer 2: (−)-[Methyl 1,4-dihydro-2,6-dimethyl-5-nitro-4-(2-trifluoromethylphenyl)-pyridine-3-carboxylate]

Isomer 3: (+)-[Methyl 4(2-benzylthiophenyl)-1,4-dihydro-2,6-dimethyl-5-nitropyridine-3-carboxylate]

Isomer 4: (−)-[Methyl 4(2-benzylthiophenyl)-1,4-dihydro-2,6-dimethyl-5-nitropyridine-3-carboxylate]

TABLE 1

| Isomer No. | Concentration (g/mol) | Change in CA (%) | Change in PP (%) |
|---|---|---|---|
| 1 | $3 \cdot 10^{-8}$ | −21 | −12 |
| 1 | $3 \cdot 10^{-7}$ | −76 | −18 |
| 2 | $3 \cdot 10^{-9}$ | +47 | +8 |
| 2 | $3 \cdot 10^{-8}$ | +86 | +20 |
| 3 | $10^{-7}$ | 0 | −15 |
| 3 | $10^{-6}$ | −26 | −31 |
| 4 | $10^{-10}$ | +2 | +22 |
| 4 | $10^{-9}$ | +106 | +20 |

CA = contraction amplitude
PP = perfusion pressure

Table 2 shows, by way of example, the contractility-boosting and coronary-dilating action of combinations on the isolated perfused heart of the guinea pig.

Combination 1: consisting of
(−)-[Methyl 1,4-dihydro-2,6-dimethyl-5-nitro-4-(2-trifluoromethylphenyl)-pyridine-3-carboxylate] and
(+)-[Methyl 1,4-dihydro-2,6-dimethyl-5-nitro-4-(2-trifluoromethylphenyl)-pyridine-3-carboxylate]
in the ratio of 1:10.

Combination 2: consisting of
(−)-[methyl 1,4-dihydro-2,6-dimethyl-5-nitro-4-(2-trifluoromethylphenyl)-pyridine-3-carboxylate] and
(+) [methyl 4-(2-benzylthiophenyl)-1,4-dihydro-2,6-dimethyl-5-nitropyridine-3-carboxylate]
in the ratio of 1:30.

| Combination | Concentrations | CA | PP |
|---|---|---|---|
| 1 | $10^{-9}/10^{-8}$ g/ml | +29% | −8% |
|   | $10^{-8}/10^{-7}$ g/ml | +48% | −17% |
| 2 | $3 \times 10^{-9}/9 \times 10^{-8}$ g/ml | +68% | −21% |
|   | $10^{-8}/3 \times 10^{-7}$ g/ml | +75% | −27% |

CA = contraction amplitude
PP = perfusion pressure

Both individual active substances and the active substance combination can be converted, in a known manner, to the customary formulations, such as tablets, capsules, dragees, pills, granules, aerosols, syrups, emulsions, suspensions and solutions, using inert, non-toxic, phamaceutically suitable carriers or solvents. The therapeutically active compounds or combinations should in each case be present in a concentration of about 0.5 to 90% by weight of the total mixture, i.e. in amounts which suffice to achieve the stated dosage range.

These formulations are prepared, for example, by extending the active substance combination or individual active substances with solvents and/or dispersants and, for example when using water as a diluent, organic solvents can, where appropriate, be used as auxiliary solvents.

As auxiliary substances there may be mentioned, for example:

Water, non-toxic organic solvents, such as paraffins (for example petroleum fractions), vegetable oils (for example ground nut oil/sesame oil), alcohols (for example ethyl alcohol and glycerol), glycols (for example propylene glycol and polyethylene glycol), solid carriers, such as, for example, natural rock powders (for example kaolins, aluminas, talc and chalk), synthetic rock powders (for example highly disperse silica and silicates), sugars (for example sucrose, lactose and glucose), emulsifiers (for example polyoxyethylene fatty acid esters, polyoxyethylene fatty alcohol ethers, alkylsulphonates and arylsulphonates), dispersants (for example lignin, sulphite waste liquors, methylcellulose, starch and polyvinylpyrrolidone) and lubricants (for example magnesium stearate, talc, stearic acid and sodium lauryl sulphate).

Administration takes place in the usual manner, preferably orally or parenterally, especially perlingually or intravenously. In the case of oral use, tablets can of course also contain, in addition to the stated carriers, additives such as sodium citrate, calcium carbonate and dicalcium phosphate together with various adjuvants, such as starch, preferably potato starch, gelatin and the like. Furthermore, lubricants, such as magnesium stearate, sodium lauryl-sulphate and talc can additionally be used to tablet-making. In the case of aqueous suspensions and/or elixiers, which are intended for oral use, the active substances or combinations can be mixed, not only with the abovementioned auxiliaries, but also with various flavour improvers or colorants.

For parenteral application, solutions of the active substance combination or of individual active substances can be employed, using suitable liquid vehicles.

PREPARATION EXAMPLES

Example 1

(a) (+)-[(S)-2-Methoxy-2-phenylethyl 1,4-dihydro-2,6-dimethyl-5-nitro-4-(2-trifluoromethyl-phenyl)-pyridine-3-carboxylate]

2.35 g (10 mmol) of (+)-[(S)-2-methoxy-2-phenylethyl 3-aminocrotonate] are heated to reflux temperature in 20 ml of i-propanol with 2.59 g (10 mmol) of 2-nitro-1-(2-trifluoromethylphenyl)-but-1-en-3-one. On rubbing, the product crystallises out from the hot solution, and is then recrystallised from hot isopropanol and filtered off while hot.

Yield: 2.1 g (44% of theory).
Melting point: 209° C. (decomp.).
Optical rotation $[\alpha]_D^{20} = +144.47°$ (dioxane).

(b) (+)-[Methyl 1,4-dihydro-2,6-dimethyl-5-nitro-4-(2-trifluoromethyl-phenyl)-pyridine-3-carboxylate]

1.19 g (2.5 mmol) of (+)-[(S)-2-methoxy-2-phenylethyl 1,4-dihydro-2,6-dimethyl-5-nitro-4-(2-trifluoromethylphenyl)pyridine-3-carboxylate] in 100 ml of methanol are heated at 50° C. for 50 hours with 270 mg of sodium methylate. The pH is then adjusted to 3 with methanolic HCl, the mixture is evaporated, and the residue is chromatographed over silica gel with 3% chloroform/methanol.

Yield: 480 mg (54% of theory).
Melting point: 177° C.
Optical rotation $[\alpha]_D^{20} = +46.8°$ (dioxane).

Example 2

(a) (−)-[(R)-2-Methoxy-2-phenylethyl 1,4-dihydro-2,6-dimethyl-5-nitro-4-(2-trifluoromethyl-phenyl)-pyridine-3-carboxylate]

2.35 g (10 mmol) of (−)[-(R)-2-methoxy-2-phenylethyl 3-aminocrotonate] are heated at reflux temperature in 20 ml of i-propanol with 2.59 g (10 mmol) of 2-nitro-1-(2-trifluoromethylphenyl)-but-1-en-3-one. After rubbing, the product crystallises from the hot solution; it is isolated from the hot solution.

Yield: 2.3 g (48% of theory).
Melting point: 208° (decomp.).
Optical rotation $[\alpha]_D^{20} = -142.47°$ (dioxane).

(b) (−)-[Methyl 1,4-dihydro-2,6-dimethyl-5-nitro-4-(2-trifluoromethyl-phenyl)-pyridine-3-carboxylate]

1.19 g (2.5 mmol) of (−)-[(R)-2-methoxy-2-phenylethyl 1,4-dihydro-2,6-dimethyl-5-nitro-4-(2-trifluoromethylphenyl)-pyridine-3-carboxylate] in 100 ml of methanol are heated at 50° C. for 3 hours with 270 mg of sodium methylate. The pH is adjusted to 3 with methanolic HCl, the mixture is evaporated and the residue is chromatographed over silica gel with chloroform +3% of methanol.

Yield: 510 mg (57% of theory).
Melting point: 176° C.
Optical rotation $[\alpha]_D^{20} = -56.7°$ (dioxane).

The following were prepared analogously to Examples 1 and 2.

Example 3

(+)-[Methyl 4-(2-benzyloxyphenyl)-1,4-dihydro-2,6-dimethyl-5-nitropyridine-3-carboxylate]

Optical rotation $[\alpha]_D^{20} = +83.5°$ (dioxane).

Example 4

(−)-[Methyl 4-(2-benzyloxyphenyl)-1,4-dihydro-2,6-dimethyl-5-nitropyridine-3-carboxylate]

Optical rotation $[\alpha]_D^{20} = -92.3°$ (dioxane).

Example 5

(+)-[Methyl 4-(2-difluoromethoxyphenyl)-1,4-dihydro-2,6-dimethyl-5-nitropyridine-3-carboxylate]

Optical rotation $[\alpha]_D^{20} = +14.7°$.

Example 6

(−)-[Methyl 4-(2-difluoromethoxyphenyl)-1,4-dihydro-2,6-dimethyl-5-nitropyridine-3-carboxylate]

Optical rotation $[\alpha]_D^{20} = -16.1°$.

Example 7

(+)-[Methyl 4-[2-(3-nitro)-benzylthio-phenyl]-1,4-dihydro-2,6-dimethyl-5-nitropyridine-3-carboxylate]

Optical rotation $[\alpha]_D^{20} = +35.2°$ (dioxane).

Example 8

(−)-[Methyl 4-[2-(3-nitro)-benzylthio-phenyl]-1,4-dihydro-2,6-dimethyl-5-nitropyridine-3-carboxylate]

Optical rotation $[\alpha]_D^{20} = -42.7°$ (dioxane).

Example 9

(+)-[Methyl 4-(2-benzylthiophenyl)-1,4-dihydro-2,6-dimethyl-5-nitropyridine-3-carboxylate]

Optical rotation $[\alpha]_D^{20} = +56.1°$ (dioxane).

Example 10

(−)-[Methyl 4-(2-benzylthiophenyl)-1,4-dihydro-2,6-dimethyl-5-nitro-pyridine-3-carboxylate]

Optical rotation $[\alpha]_D^{20} = -58.4°$.

Example 11

(+)-[Methyl 1,4-dihydro-2,6-dimethyl-5-nitro-4-(5-pyrimidyl)-pyridine-3-carboxylate]

Optical rotation $[\alpha]_{546}^{20} = +37.7°$ (acetone).

Example 12

(−)-[Methyl 1,4-dihydro-2,6-dimethyl-5-nitro-4-(5-pyrimidyl)-pyridine-3-carboxylate]

Optical rotation $[\alpha]_{546}^{20} = -39.1°$ (acetone).

Example 13

(−)-1,4-Dihydro-2,6-dimethyl-5-nitro-4-(2-trifluoromethylphenyl)-pyridine-3-carboxylic acid 1.19 g (2.5 mmol) of (+)-[(S)-2-methoxy-2-phenylethyl 1,4-dihydro-2,6-dimethyl-5-nitro-4-(2-trifluoromethylphenyl)pyridine-3-carboxylate] in 100 ml of methanol are heated at 40° C. for 15 hours with 300 mg of sodium hydroxide. The mixture is then evaporated, and the residue is taken up in chloroform and washed with twice 20 ml of water. The pH of the aqueous phase is adjusted slowly to 3 with dilute HCl; the product crystallises out and is filtered off with suction.

Yield: 320 mg (37% of theory).
Melting point: 218° C. (decomp.).
Optical rotation: $[\alpha]_{546}^{20} = -10.6°$ (acetone).

Example 14

(+)-1,4-Dihydro-2,6-dimethyl-5-nitro-4-(2-trifluoromethylphenyl)-pyridine-3-carboxylic acid 1.19 g (2.5 mmol) of (−)-[(R)-2-methoxy-2-phenylethyl 1,4-dihydro-2,6-dimethyl-5-nitro-4-(2-trifluoromethylphenyl)pyridine-3-carboxylate] in 100 ml of methanol are heated at 40° C. for 15 hours with 300 mg of sodium hydroxide. The mixture is then evaporated, and the residue is taken up in chloroform and washed with twice 20 ml of water. The pH of the aqueous phase is adjusted slowly to 3 with dilute HCl; the product crystallises out and is filtered off with suction.

Yield: 345 mg (40% of theory).
Melting point: 217° C. (decomp.).
Optical rotation: $[\alpha]_{546}^{20} = +11.5°$ C. (acetone).

Example 15

(−)-1,4-Dihydro-2,6-dimethyl-3-nitro-4-(2-trifluoromethylphenyl)-pyridine 171 mg (0.5 mmol) of (−)-1,4-dihydro-2,6-dimethyl-5-nitro-4-(2-trifluoromethylphenyl)-pyridine-3-carboxylic acid in 10 ml of methanol are heated to the reflux temperature for 7 hours with 100 mg of concentrated sulphuric acid. The mixture is then diluted with 50 ml of H$_2$O. The precipitated product is filtered off with suction and recrystallised from i-propanol.

Yield: 122 mg (82% of theory).
Melting point: 210° C.
Optical rotation: $[\alpha]_D^{20} = -583°$ (acetone).

Example 16

(+)-1,4-Dihydro-2,6-dimethyl-3-nitro-4-(2-trifluoromethylphenyl)-pyridine 171 mg (0.5 mmol) of (+)-1,4-dihydro-2,6-dimethyl-5-nitro-4-(2-trifluoromethylphenyl)-pyridine-3-carboxylic acid in 10 ml of methanol are heated to the reflux temperature for 7 hours with 100 mg of concentrated sulphuric acid. The mixture is then diluted with 50 ml of H$_2$O. The precipitated product is filtered off with suction and recrystallised from i-propanol.

Yield: 114 mg (76% of theory).
Melting point: 211° C.
Optical rotation: $[\alpha]^{20} = -587°$ (acetone).

Example 17

(−)-[3-Bromopropyl 1,4-dihydro-2,6-dimethyl-5-nitro-4-(2-trifluoromethylphenyl)-pyridine-3-carboxylate]

700 mg (5 mmol) of 3-bromopropanol and 123 mg (0.6 mmol) of dicyclohexylcarbodiimide are added at room temperature to 171 mg (0.5 mmol) of (+)-1,4-dihydro-2,6-dimethyl-5-nitro-4-(2-trifluoromethylphenyl)-pyridine-3-carboxylic acid in 15 ml of tetrahydrofuran. After the solvent has been removed by evaporation, the residue is chromatographed over silica gel, using chloroform.

Yield: 104 mg (45% of theory).
Optical rotation: $[\alpha]^{20} = 42.46$ (dioxane).

We claim:

1. A mixture of (a) pure enantiomer and (b) 0.01 to 1000 times the weight of (a) of another pure enantiomer or physiologically acceptable salts thereof, except for racemates and diastereomers, of a 5-nitrodihydropyridine of the formula

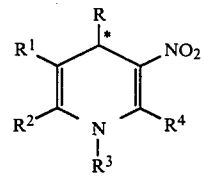

in which

R represents pyridyl or pyrimidyl, or represents phenyl which is optionally monosubstituted or disubstituted, identically or differently, by fluorine, chlorine, nitro or cyano or by C$_1$-C$_4$-alkyl or C$_1$-C$_4$-alkoxy which is optionally substituted by one or more fluorine atoms, or by the group

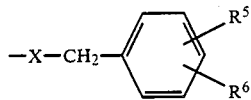

wherein

X represents oxygen or sulphur and $R^5$ and $R^6$ are identical or different and represent hydrogen, nitro, cyano or $C_1$-$C_2$-alkyl, $C_1$-$C_2$-alkoxy, $C_1$-$C_2$-alkylthio, halogeno-$C_1$-$C_2$-alkyl and halogeno-$C_1$-$C_2$-alkoxy, $R^1$ represents hydrogen or the group $CO_2R^8$, wherein $R^8$ represents hydrogen or linear or branched $C_1$-$C_8$-alkyl which can be interrupted in the chain by an oxygen and/or sulphur atom and which can optionally be substituted by phenyl, nitro, or one or more fluorine, chlorine, bromine, hydroxyl, cyano, —$SO_2$-alkyl having up to 2 C-atoms, $C_1$-$C_2$-alkoxycarbonyl or pyridyl groups or by an amino group, it being possible for this amino group to be substituted by one or two substituents from the series $C_1$-$C_3$-alkyl, phenyl or benzyl, $R_2$ and $R_4$ represent methyl or ethyl which is optionally substituted by hydroxyl or one or more fluorine groups and $R^3$ represents hydrogen or methyl or ethyl, one of the enantiomers having a high vasodilative action and a low negative inotropic activity on heart muscle, the other enantiomer having a low vasoconstrictive action and a high positive inotropic activity on heart muscle, the mixture being high in vasodilative activity and in positive inotropic activity on heart muscle.

2. A mixture according to claim 1, wherein one of the enantiomers is (+)-[methyl 1,4-dihydro-2,6-dimethyl-5-nitro-4-(2-trifluoromethylphenyl)-pyridine-3-carboxylate].

3. A mixture according to claim 1, wherein one of the enantiomers is (—)-[methyl 1,4-dihydro-2,6-dimethyl-5-nitro-4-(2-trifluoromethylphenyl)-pyridine-3-carboxylate].

4. A mixture according to claim 1, wherein one of the enantiomers is (+)-[methyl 4-(2-benzylthiophenyl)-1,4-dihydro-2,6-dimethyl-5-nitropyridine-3-carboxylate].

5. A mixture according to claim 1, wherein one of the enantiomers is (—)-[methyl 4-(2-benzylthiophenyl)-1,4-dihydro-2,6-dimethyl-5-nitropyridine-3-carboxylate].

6. A mixture of (a) pure (—)-enantiomer of methyl 1,4-dihydro-2,6-dimethyl-5-nitro-4-(2-trifluoromethylphenyl)-pyridine-3-carboxylate and several times its weight of (b) pure (+)-enantiomer of methyl 1,4-dihydro-2,6-dimethyl-5-nitro-4-(2-trifluoromethylphenyl)-pyridine-3-carboxylate.

7. A mixture of (a) pure (—)-enantiomer of methyl 1,4-dihydro-2,6-dimethyl-5-nitro-4-(2-trifluoromethylphenyl)-pyridine-3-carboxylate and several times its weight of (b) pure (+)-enantiomer of methyl 4-(2-benzylthiophenyl)-1,4-dihydro-2,6-dimethyl-5-nitropyridine-3-carboxylate.

* * * * *